(12) United States Patent
Wang et al.

(10) Patent No.: US 11,835,608 B1
(45) Date of Patent: Dec. 5, 2023

(54) SHIELD-FREE MRI SYSTEM OF TIME-VARYING ELECTROMAGNETIC FIELDS IN COMPLEX ELECTROMAGNETIC ENVIRONMENTS

(71) Applicant: Zepp Europe Holding B.V., Amsterdam-Duivendrecht (NL)

(72) Inventors: Jinghua Wang, Cupertino, CA (US); Kongqiao Wang, Anhui (CN); Li Guo, Anhui (CN)

(73) Assignee: Zepp Europe Holding B.V., Amsterdam-Duivendrecht (NL)

( * ) Notice: Subject to any disclaimer, the term of this patent is extended or adjusted under 35 U.S.C. 154(b) by 0 days.

(21) Appl. No.: 17/843,431

(22) Filed: Jun. 17, 2022

(51) Int. Cl.
| | |
|---|---|
| *G01R 33/42* | (2006.01) |
| *G01R 33/422* | (2006.01) |
| *G01R 33/385* | (2006.01) |
| *A61B 5/055* | (2006.01) |
| *G01R 33/36* | (2006.01) |
| *G01R 33/28* | (2006.01) |
| *G01R 33/3815* | (2006.01) |

(52) U.S. Cl.
CPC ............ *G01R 33/422* (2013.01); *A61B 5/055* (2013.01); *G01R 33/288* (2013.01); *G01R 33/3614* (2013.01); *G01R 33/3815* (2013.01); *G01R 33/3852* (2013.01); *G01R 33/3854* (2013.01)

(58) Field of Classification Search
CPC ................ G01R 33/422; G01R 33/288; G01R 33/3614; G01R 33/3815; G01R 33/3852; G01R 33/3854; A61B 5/055
See application file for complete search history.

(56) References Cited

U.S. PATENT DOCUMENTS

| | | | |
|---|---|---|---|
| 8,427,152 B2 | 4/2013 | Ren et al. | |
| 9,788,413 B2 | 10/2017 | Moseri et al. | |
| 10,191,127 B2 | 1/2019 | Strauss et al. | |
| 10,794,975 B2 | 10/2020 | Rapoport et al. | |
| 2017/0108569 A1* | 4/2017 | Harvey | G01R 33/36 |
| 2019/0159733 A1 | 5/2019 | Shusterman | |
| 2020/0058106 A1 | 2/2020 | Lazarus et al. | |
| 2020/0294287 A1* | 9/2020 | Schlemper | G06V 10/454 |
| 2021/0100474 A1 | 4/2021 | Dyvorne et al. | |
| 2021/0103017 A1 | 4/2021 | Dyvorne et al. | |

FOREIGN PATENT DOCUMENTS

| | | |
|---|---|---|
| WO | 2012048621 A1 | 4/2012 |
| WO | 2020037121 A1 | 2/2020 |
| WO | 2021071938 A2 | 4/2021 |
| WO | 2021/217135 A1 | 10/2021 |

* cited by examiner

Primary Examiner — G. M. A Hyder
(74) Attorney, Agent, or Firm — Young Basile Hanlon & MacFarlane, P.C.

(57) ABSTRACT

The present disclosure relates to a method and a system for minimizing electromagnetic interference (EMI) of magnetic resonance imaging (MRI) systems in complex electromagnetic environments. The method and system described herein provide superior MRI image quality and may reduce costs by eliminating the requirement of expensive shielding in MRI systems/hybrid MRI systems.

20 Claims, 5 Drawing Sheets

SHIELD-FREE MRI SYSTEM OF TIME-VARYING ELECTROMAGNETIC FIELDS IN COMPLEX ELECTROMAGNETIC ENVIRONMENTS

CROSS-REFERENCE TO RELATED APPLICATION(S)

None.

FIELD OF THE INVENTION

The present disclosure relates to a method and a system for minimizing electromagnetic interference (EMI) of magnetic resonance imaging (MRI) systems in complex electromagnetic environments. The method and system described herein provide superior MRI image quality and may reduce costs by eliminating the requirement of expensive shielding of MRI systems in complex electromagnetic environments.

DESCRIPTION OF THE RELATED ART

Many diseases such as, for example, cancer, cardiovascular disease, liver disease, inflammatory disease (e.g., Crohn's disease, ulcerative colitis, etc.) and detrimental body conditions (e.g., spinal degeneration, nerve injuries, ligament damage, etc.) can be diagnosed by MRI systems, which provide images that may illustrate differences between healthy tissue and lesions. MRI is a safer technology than, for example, x-ray, computed tomography (CT) or positron emission technology (PET) because patients and medical personnel are not subjected to ionizing radiation exposure during the imaging procedure.

Every year, more than 35 million MRI scans are performed in the United States and more than 70 million MRI scans are performed worldwide to diagnose various disease and detrimental conditions, supra. A high-quality scan is necessary to maximize diagnostic sensitivity and accuracy. Generally, high quality images are characterized by high signal to noise ratio (SNR), high contrast between normal tissue and lesion, minimal artifacts, and appropriate spatial-temporal resolution.

A subject is positioned in a homogeneous static magnetic field so that the nuclear spins of the subject generate net magnetization oriented along the static magnetic field to provide a detectable magnetic resonance (MR) signal. The net magnetization is rotated away from the static magnetic field using a radio frequency (RF) excitation field with the same frequency as the Larmor frequency of the nucleus. The angle of rotation is determined by the field strength and duration of the RF excitation pulse. At the end of the RF excitation pulse, the nuclei, in relaxing to their normal spin conditions, generate a decaying MR signal. The MR signal is collected by a receiver coil, amplified, and processed. The acquired measurements, which are collected in the spatial frequency domain, are digitized, and stored as complex numerical values in a "k-space"matrix. An image can be reconstructed from the k-space data, for example, by an inverse 2D or 3D fast Fourier transformation (FFT) from the raw k-space data.

EMI negatively affects MRI operation and image quality. For example, EMI from external sources such as, for example, electric lines, television and radio signals, lights and elevators, in the vicinity of a MRI scanner, may negatively impact the quality of acquired images. Conventionally, fixed or mobile MRI scanners are shielded using a Faraday cage or a shielded room to attenuate time-varying electromagnetic field to isolate the MRI system from EMI. In the absence of electromagnetic shielding, EMI from external sources may cause artifacts (e.g., horizontal or vertical lines) in the image.

Additionally, electronic devices (such as lights, heating system, PET system, supply lines, gradient coil effects, radiofrequency amplifier, gradient amplifier, electrical surgical devices, robotic, etc.) are frequently located with MRI systems in a shielded location. The EMI introduced by these electronic devices,(i.e., internal sources), negatively affects MRI operation and image quality.

The effect of EMI on MRI signals becomes more complex for portable MRI and hybrid MRI systems. For example, electromagnetic shielding in a portable MRI system is limited by space and a complex electromagnetic environment. Accordingly, additional electromagnetic shielding must be introduced to attenuate the effect of EMI from adjacent electronic devices on image quality during a portable MRI scanner operation. Additionally, the effect of EMI from internal resources is usually reduced by filters and shielding of internal electric devices.

However, there is a still a need for MRI systems which inexpensively reduce EMI in complex electromagnetic environments.

SUMMARY

The present application satisfies these and other needs by providing methods and systems for minimizing EMI of MRI systems in complex electromagnetic environments. The method and system described herein provide superior MR image quality and may reduce costs by eliminating the requirement of expensive shielding of MRI systems in complex electromagnetic environments.

In one aspect, an MRI system for minimizing EMI in an image acquired by the MRI system is provided. The MRI system includes a magnet, one or more RF gradient coils, one or more MRI signal receiving coils, one or more EMI detectors which include electrically conductive coils adjacent to at least one of the RF gradient coils and the EMI detectors adjacent to the MRI signal receiving coils, and a computing device which acquires a plurality of k-space data by the one or more MRI signal receiving coils using one or more MRI sequences, simultaneously acquires EMI data from the one or more EMI detectors corresponding to each of the plurality of k-space data, minimizes the effect of EMI on the k-space data by reducing the EMI data from the k-space data using an MRI physics-based model-to provide corrected k-space data, reconstructs the image from the corrected k-space data and obtains the image with minimized EMI.

In another aspect, a method for minimizing electromagnetic interference (EMI) in an image acquired by a MRI system at a static magnetic field is provided. The method includes the steps of including one or more gradient coils, one or more MRI signal receiver coils, one or more EMI detectors which include electrically conductive coils adjacent to at least one or more of the RF gradient coils and adjacent to the MRI signal receiving coils, including a subject in a magnet bore of the MRI system, acquiring a plurality of k-space data of the subject by the one or more MRI signal receiver coils using one or more MRI sequences, simultaneously acquiring EMI data from the one or more EMI detectors corresponding to each of the plurality of k-space data, minimizing the effect of EMI on the k-space data by reducing the EMI data from the k-space data using an MRI physics-based model to provide corrected k-space data, reconstructing the from the corrected k-space data; and obtaining the image with minimized EMI.

BRIEF DESCRIPTION OF DRAWINGS

The disclosure is best understood from the following detailed description when read in conjunction with the accompanying drawings. It is emphasized that, according to common practice, the various features of the drawings are not to scale. On the contrary, the dimensions of the various features are arbitrarily expanded or reduced for clarity.

DETAILED DESCRIPTION

1. Definitions

Figure 1:
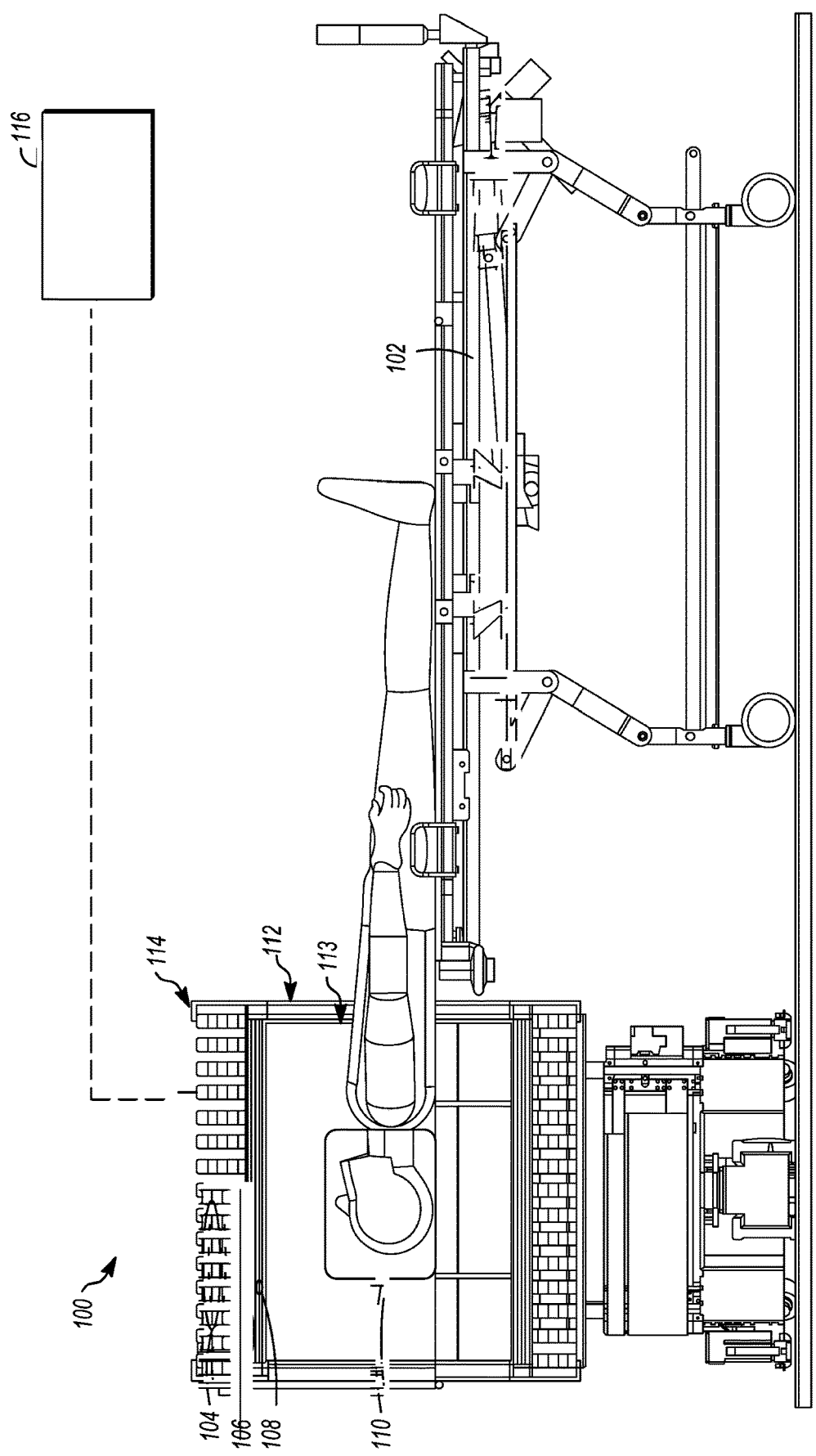
FIG. 1 is a diagram illustrating an example of an MRI system.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising," and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not.

The term "artifact" and its variations herein are defined as a false feature which is not present in the original object in the MR image. The artifacts may affect the diagnostic quality, leading to the confusion with pathology. Artifacts can be classified as patient-related, signal processing-dependent and hardware-related.

The term "EMI" and its variations herein are defined as an interference that usually results from electromagnetic radiation, electromagnetic induction, or a combination thereof may be an interference that is derived from any source natural or artificial, for example, supply lines, gradient coil effects, atmospheric noise, truck, electrical lines, subways, cellular communication equipment, electrical devices, TV and radio stations, elevators, and so on. EMI can distort the magnetic field uniformity, and change the transmitted and received RF signals, therefore resulting in either artifacts or missing information of the images acquired with an MRI system.

The term "internal EMI" and its variations herein are defined as a noise or a feature of time-varying electromagnetic interference that always is inside of the shielded MRI scanner room or a Faraday cage around the MRI system. The internal electromagnetic interference can be caused from one or more of the lights, heating system, PET system, supply lines, gradient coil effects, radiofrequency amplifier, gradient amplifier, electrical surgical devices, robotic and other electric devices. In particular, many electronic medical devices operating in a shielded room or space during MRI-guided surgery and treatments generate considerable EMI. In a shielded room or space, the unwanted internal EMI, is always present in a RF receiver in addition to the desired MRI signal, leading to artifacts or increased noise. Accordingly, there is a still a need to reduce the effect of internal EMI on MRI signals in complex electromagnetic environments, particularly in presence of many additional electronic devices in a shielded MRI scanner room.

The term "external EMI" and its variations herein are defined as an electromagnetic interference from the outside of the shield MRI scanner room or a Faraday cage that usually results from electromagnetic radiation, electromagnetic induction, or a combination. In particular, external EMI is associated with an MRI system without the perfect shielding of a time-varying electromagnetic field (i.e., without shielding or with partial shielding). The external EMI is derived from any source, either natural or artificial, for example, atmospheric noise, truck, electrical lines, subways, cellular communication equipment, electronic devices, TV and radio stations, elevators, etc. The external EMI can change the transmitted and received RF signals, therefore resulting in either artifacts or missing information of the images acquired with an MRI system.

The term "hybrid MRI system" and its variations herein are defined as image acquisitions on systems that physically combine complementary imaging modalities for an improved diagnostic accuracy and confidence as well as for increased patient comfort for example positron emission tomography - magnetic resonance imaging (PET-MRI) scan or magnetic resonance imaging guided linear accelerator (MRI-LINAC).

2. Implementations

In some implementations, an MRI system for minimizing EMI in an image acquired by the MRI system is provided. The MRI system includes a magnet, one or more RF gradient coils, one or more MRI signal receiving coils, one or more EMI detectors which include electrically conductive coils adjacent to at least one or more of the RF gradient coils and the EMI detectors adjacent to the MRI signal receiving coils, and a computing device which acquires a plurality of k-space data by the one or more MRI signal receiving coils using one or more MRI sequences, simultaneously acquires EMI data from the one or more EMI detectors corresponding to each of the plurality of k-space data, minimizes the effect of EMI on the k-space data by reducing the EMI data from the k-space data using an MRI physics-based model-to provide corrected k-space data, reconstructs the image from the corrected k-space data and obtains the image with minimized EMI.

In some implementations, the EMI is an internal EMI from electronic devices inside an electromagnetically shielded room. In other implementations, the subject is a mammal, a human, an object or a phantom.

In some implementations, the MRI system includes a superconducting magnet. In other implementations, the MRI system is portable, mobile, or stationary. In still other implementations, the static magnetic strength of the MRI system is less than about 0.01 Tesla, less than about 0.1 Tesla, less than about 0.3 Tesla, less than about 1.0 Tesla, less than about 1.5 Tesla or less than about 7.0 Tesla.

In some implementations, the EMI detectors adjacent to the RF gradient coils and the EMI detectors adjacent to the MRI signal receiving coils include least one inside and at least one outside of the imaging volume. In other implementations, the coils of the EMI detectors adjacent to the MRI signal receiving coils is mechanically adjusted to increase correlation and reduce induction between the EMI detectors and the MRI signal receiving coils. In still other implementations, the angle between the axis of the coils of the EMI and the direction of the static magnetic field is close to 90 degrees. In still other implementations, the coils of the EMI detector adjacent to the MRI signal receiving coils is different from the MRI signal receiving coils in coil number, coil size, loop number and decoupling.

In some implementations, the MRI physics-based model is determined by the Bloch Equation and its variations. In other implementations, minimizing the effect of EMI by a neural network comprises pre-scanning the EMI k-space data and MRI k-space data for a phantom, applying a general neural network model for minimizing EMI, refining the general neural network model using transfer learning and the data from pre-scanning to obtain an optimal neural network model; and minimizing the effect of EMI by the optimal neural network model.

In some implementations, the imaging volume is enclosed by the EMI detectors.

In some implementations, the frequencies of the EMI data are similar to the Larmor frequencies. In other implementations, the frequencies are between about 1.0 MHz and about 960 MHz.

In some implementations, the EMI data comprises internal EMI data and external EMI data. In other implementations, external EMI data is minimized by real time EMI data.

In some implementations, a method for minimizing electromagnetic interference (EMI) in an image acquired by a MRI system at a static magnetic field is provided. The method includes the steps of including one or more gradient coils, one or more MRI signal receiver coils, one or more EMI detectors which include electrically conductive coils adjacent to at least one of the RF gradient coils and the MRI signal receiving coils, including a subject in a magnet bore of the MRI system, acquiring a plurality of k-space data of the subject by the one or more MRI signal receiver coils using one or more MRI sequences, simultaneously acquiring EMI data from the one or more EMI detectors corresponding to each of the plurality of k-space data, minimizing the effect of EMI on the k-space data by reducing the EMI data from the k-space data using an MRI physics-based model to provide corrected k-space data, reconstructing the from the corrected k-space data and obtaining the image with minimized EMI.

In some implementations the EMI is an internal EMI resulting from electronic devices inside an electromagnetically shielded room. In other implementations the magnet is a superconducting magnet. In still other implementations, the MRI physics-based model is determined by the Bloch Equation and its variations. In still other implementations, the MRI physics-based model is a neural network which comprises pre-scanning the EMI k-space data and MRI k-space data for a phantom, applying a general neural network model for minimizing EMI, refining the general neural network model using transfer learning and the data from pre-scanning to obtain an optimal neural network model; and minimizing the effect of EMI by the optimal neural network model.

3. Imaging System

FIG. 1 is an exemplary diagram illustrating an MRI system 100 with a vertical Bo and a horizontal Bi at the static field strength of less than 0.1 Tesla. However, the static magnetic field of MRI system 100 may be different for different magnets, for example, less than about 0.1 Tesla and less than about 0.3 Tesla for both an electromagnetic magnet and a permanent magnet, less than about 1.0 Tesla for both a permanent magnet and superconductive magnet, less than 1.5 Tesla for a superconductive magnet, or less than about 7.0 Tesla for a superconductive magnet. The MRI system 100 may be portable, mobile or stationary and is usable with any table 102 on which a subject may reside (e.g., a mammal, human, object or phantom). The table 102 may be raised or lowered to a height of the system 100 or the system 100 may be raised or lowered to a height of the table 102. The system 100 includes a permanent magnet 104, which may be a superconducting magnet. The permanent magnet 104 surrounds the patient while the patient is located in a magnet bore 113 of the permanent magnet 104. The permanent magnet 104 may work in conjunction with RF gradient coils 106 and is encased .

The gradient coils 106 may assist the permanent magnet 104 in creating an electric linear field. The electric field (e.g., a strong static magnetic field) may be created in any direction of an x, y, z, coordinate system for spatial encoding. The system 100 includes a radio transmission coil (RF TX coil) 108 which transmits electric fields excite nuclear spins. A MRI signal reception coil 110 receives the MRI signal that is introduced by the nuclear spin precession. A plurality of k-space data is acquired by the MRI signal reception coil for the portion of the subject in an imaging volume using one or more MRI sequences while the subject is located in the interior 112 of the system 100.

The magnet bore 113 of the portable system 100 may be sufficiently large to fit all or a portion of a human. The magnet bore 113 may have a length that is about 1 m or more, about 1.25 m or more, about 1.5 m or more, or about 1.75 m or more. The magnet bore 113 may have a length that is about 2.5 m or less, about 2.25 m or less, or about 2 m or less. The magnet bore 113 may have cross-sectional length (e.g., diameter) of about 0.5 m or more, about 0.75 m or more, or about 1 m or more. The magnet bore 113 may have a cross-sectional length of about 2 m or less, about 1.5 m or less, or about 1.25 m or less. The cross-section of the system 100 may be symmetrical, asymmetrical, circular, oval, geometric, nongeometric, or a combination thereof. The magnet bore 113 of the system may be spaced apart from the exterior 114 by walls of the portable system 100. The magnet bore 113 may be an interior of the system. The magnet bore 113 may receive all or a portion of a subject. The magnet bore 113 may include a shutter that is either opened or closed. A computing device 116 is connected to the system 100 to control the system and provide feedback to a user.

Figure 2:
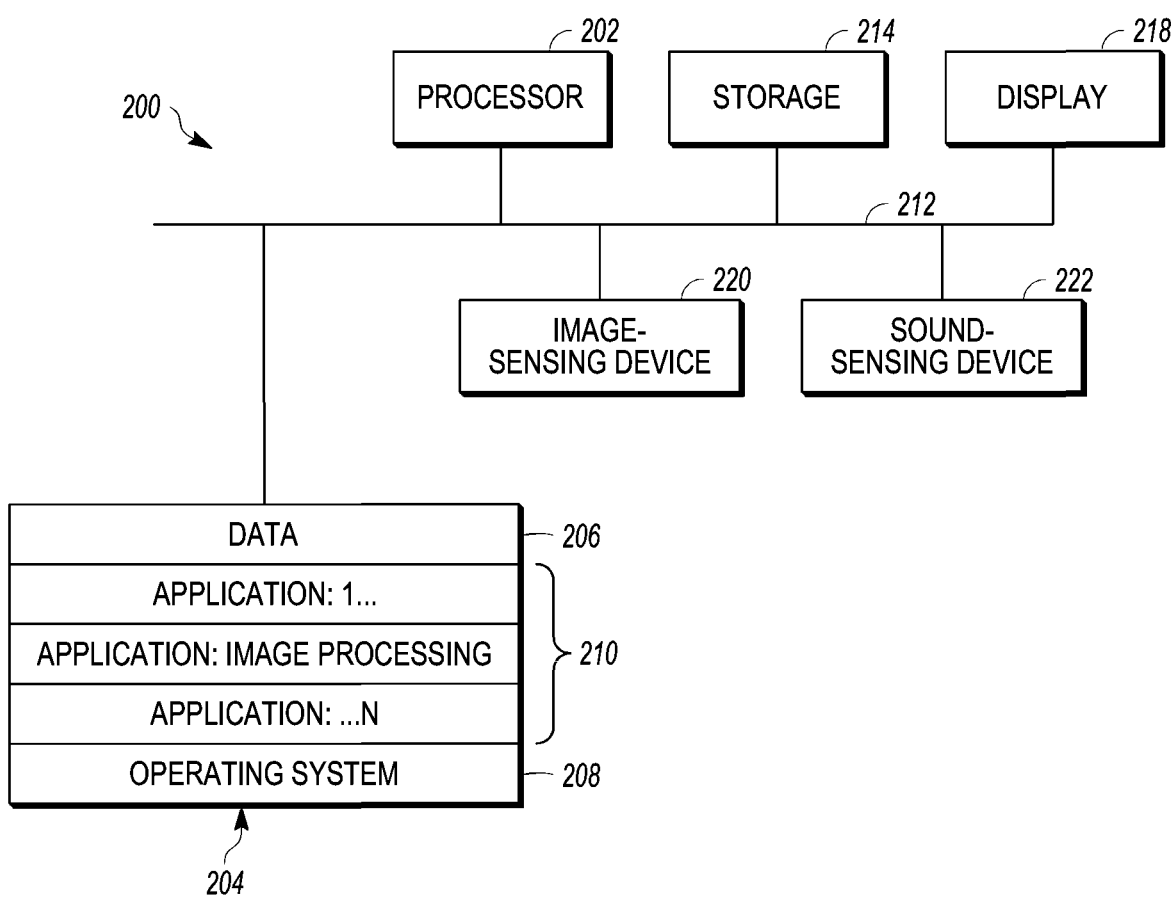
FIG. 2 is a block diagram of an example of a computing device of an MRI system of the present disclosure.

FIG. 2 is a block diagram of an example of a computing device 200. The computing device 200 can be in the form of a computing system including multiple computing devices 200, or in the form of a single computing device 200, for example, a mobile phone, a tablet computer, a laptop computer, a notebook computer, a desktop computer, the like, or a combination thereof. The computing device 200 can be communicatively connected to an MRI system, for example, to receive images from the MRI system or to control aspects of the MRI system.

A CPU 202 in the computing device 200 can be a central processing unit. Alternatively, the CPU 202 can be any other type of device, or multiple devices, capable of manipulating or processing existing information or hereafter developed. Although the disclosed implementations can be practiced with a single processor as shown, e.g., the CPU 202, advantages in speed and efficiency can be achieved using more than one processor.

A memory 204 in the computing device 200 can be a read-only memory (ROM) device or a random-access memory (RAM) device in an implementation. Any other suitable type of storage device can be used as the memory 204. The memory 204 may be flash memory, read only memory, or both. The memory 204 can include code and data 206 that is accessed by the CPU 202 using a bus 212. The memory 204 can further include an operating system 208 and application programs 210, the application programs 210 including at least one program that permits the CPU 202 to perform the methods described here. For example, the application programs 210 can include applications 1 through N, which further include an image processing application that can be used enhance, view, process, or the like, images obtained from an MRI system or an application for controlling aspects of the MRI machine. The computing device 200 can also include a secondary storage 214, which can, for example, be a memory card used with a computing device 200 that is mobile.

The computing device 200 can also include one or more output devices, such as a display 218. The display 218 can be, in one example, a touch sensitive display 218 that combines a display 218 with a touch sensitive element that is operable to sense touch inputs. The display 218 can be coupled to the CPU 202 via the bus 212. Other output devices that permit a user to program or otherwise use the computing device 200 can be provided in addition to or as an alternative to the display 218. When the output device is or includes a display 218, the display 218 can be implemented in various ways, including by a liquid crystal display (LCD), a cathode-ray tube (CRT) display or light emitting diode (LED) display, such as an organic LED (OLED) display.

The computing device 200 can also include or be in communication with an image-sensing device 220, for example a camera, or any other image-sensing device 220 now existing or hereafter developed that can sense an image such as the image of a user operating the computing device 200. The image-sensing device 220 can be positioned such that it is directed toward the user operating the computing device 200. In an example, the position and optical axis of the image-sensing device 220 can be configured such that the field of vision includes an area that is directly adjacent to the display 218 and from which the display 218 is visible.

The computing device 200 can also include or be in communication with a sound-sensing device 222, for example a microphone, or any other sound-sensing device now existing or hereafter developed that can sense sounds near the computing device 200. The sound-sensing device 222 can be positioned such that it is directed toward the user operating the computing device 200 and can be configured to receive sounds, for example, speech or other utterances, made by the user while the user operates the computing device 200.

Although FIG. 2 depicts the CPU 202 and the memory 204 of the computing device 200 as being integrated into a single unit, other configurations can be utilized. The operations of the CPU 202 can be distributed across multiple machines (each machine having one or more of processors) that can be coupled directly or across a local area or other network. The memory 204 can be distributed across multiple machines such as a network-based memory or memory in multiple machines performing the operations of the computing device 200. Although depicted here as a single bus, the bus 212 of the computing device 200 can be composed of multiple buses. Further, the secondary storage 214 can be directly coupled to the other components of the computing device 200 or can be accessed via a network and can comprise a single integrated unit such as a memory card or multiple units such as multiple memory cards. The computing device 200 can thus be implemented in a wide variety of configurations.

4. Minimizing Electromagnetic Interference of MRI Systems in a complex electromagnetic environment MRI systems require shielding from external sources of time-varying electromagnetic fields and internal electric devices (such as radiofrequency amplifier and gradient amplifier) in order to enhance image quality (such as increased signal-to-noise ratio and reduced artifacts). Conventional MRI systems typically are typically deployed in a shielded room and use filters to isolate undesirable sources of EMI and the electromagnetic noise from internal and external environments. However, not all electronic devices used with an MRI system can be placed outside of the protective shield of the scanning room or enclosed space. For example, an electric contrast agent injection system, must be located adjacent to the patient. Additionally, in hybrid PET/MRI systems, electronic portions of the PET system are combined with the MRI system. The EMI from these sources can degrade the image quality of images acquired with the MRI system.

The methods and system described herein can be used with electromagnetic, permanent and superconducting MRI systems. The method and system describe herein can also be used with both mobile and non-mobile MRI systems, including hybrid systems with robotically controlled surgical systems, hybrid MRI-PET system, hybrid MRI system with electromagnetic stimulation, etc., in complex electromagnetic environments which may result from the medical electric devices (i.e., surgical robot, electric injector, etc.) which are associated with the MRI system in an shielded room or space Minimization of EMI is performed by MRI physics-based models or neural networks in the present disclosure. The system and method described herein use a neural network in both k-space and image domain. The neural network integrates EMI correction and FFT into a neural network to output an image directly and realizes non-linear Fourier transform between spatial and frequency domains in the k-space domain.

The effect of different EMI on different MRI signals (i.e., transmission and reception) are addressed by the method and system provided herein. These effects may be evaluated by objective functions that are determined by the Bloch Equation and its variations.

The present disclosure divides EMI into internal EMI and external EMI, which are both minimized. In addition, different methods (size, receiver bandwidth, sampling time, orientation, location, etc.,) may be used to sample internal EMI signals and external EMI signals respectively in the method and system described herein.

The present disclosure evaluates and minimizes the effect of EMI on the RF transmission in a MRI system, particularly when the EMI frequency is very close to the resonant frequency in MRI system. Accordingly, in the method and system described herein, EMI detectors may detect EMI signals during both radiofrequency transmission and reception. Therefore, the present disclosure may provide better correction of EMI in the k-space domain.

Figure 3:
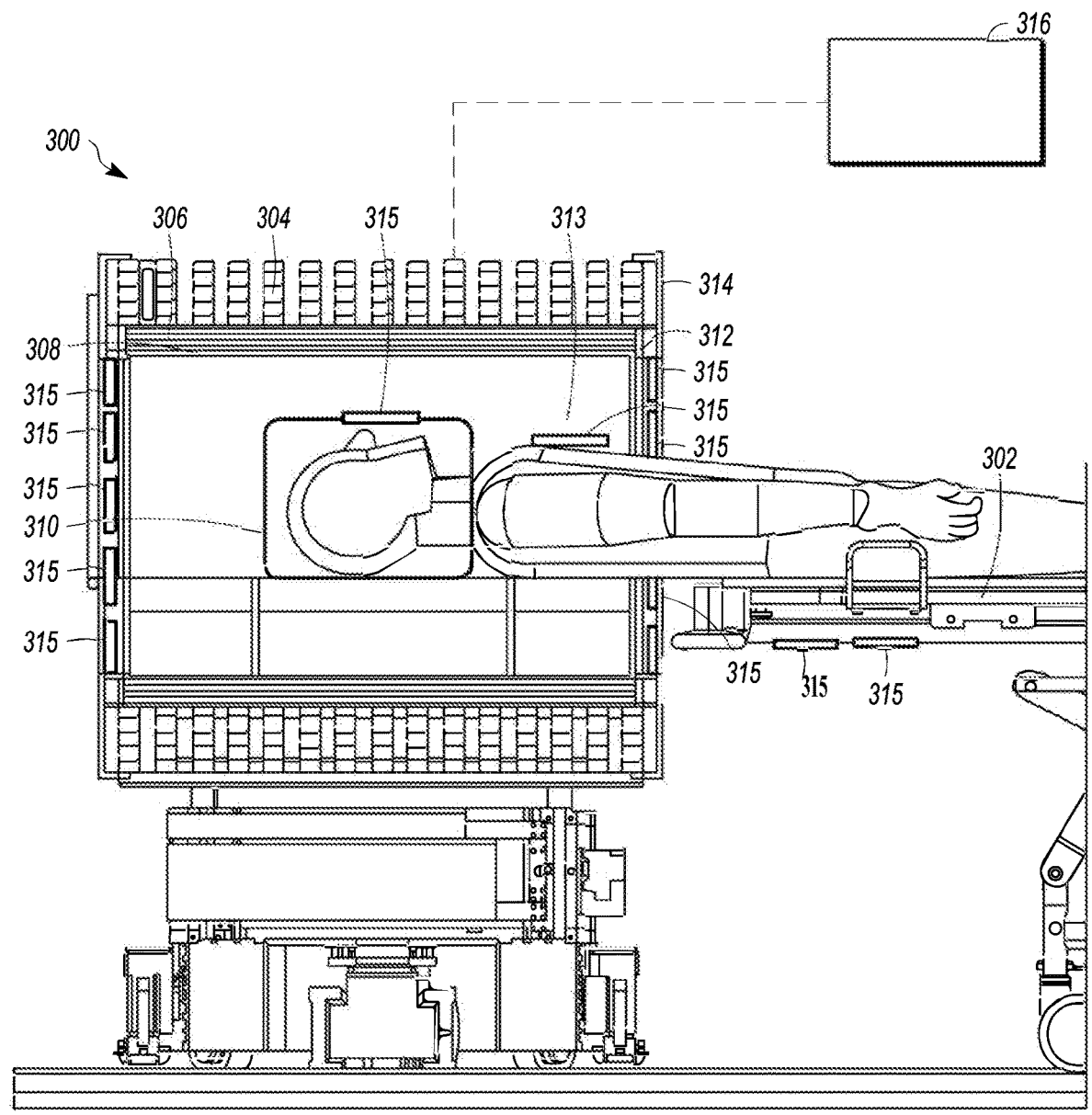
FIG. 3 illustrates an MRI system for detecting EMI using electrically conductive coils.

FIG. 3 is an exemplary diagram illustrating an MRI system 300 with a vertical $B_0$ and a horizontal $B_1$ at the static field strength of less than 0.1 Tesla with EMI detectors 315 The static magnetic field of MRI system 300 may be different for different magnets, for example, less than about 0.1 Tesla and less than about 0.3 Tesla for both an electromagnetic magnet and a permanent magnet, less than about 1.0 Tesla for both a permanent magnet and superconductive magnet, less than 1.5 Tesla for a superconductive magnet, or less than about 7.0 Tesla for a superconductive magnet. The MRI system 300 may be portable, mobile or stationary and is usable with any table on which a subject may reside (e.g., a mammal, human, object or phantom). The table 302 may be raised or lowered to a height of the system 300 or the system 400 may be raised or lowered to a height of the table 302. The system 300 includes a permanent magnet 304, which may be a superconducting magnet. The permanent magnet 304 surrounds the patient while the patient is located in a magnet bore 313 of the permanent magnet 304. The permanent magnet 304 may work in conjunction with gradient coils 306.

The gradient coils 306 may assist the permanent magnet 304 in creating an electric linear field. The electric field (e.g., a strong static magnetic field) may be created in any direction of an x, y, z, coordinate system for spatial encoding. The system 300 includes a radio transmission coil (RF TX coil) 308 which transmits electric fields excite nuclear spins. A MRI signal reception coil 310 receives the MRI signal that is introduced by the nuclear spin precession. A plurality of k-space data is acquired by the MRI signal reception coil for the portion of the subject in an imaging volume using one or more MRI sequences while the subject is located in the interior 312 of the system 300.

Positioned, for example, on the table 302 are EMI detectors 315 which acquire EMI data corresponding to each of the plurality of k-space data of the image. Note that the position of the EMI detectors 315 is variable. For example, EMI detectors 315 are inside the magnet on the magnet, inside the imaging volume or outside on table 302. The EMI data may be internal EMI data or external EMI data and the external EMI data may be minimized by the real time EMI data. The EMI detectors 315 may be inside or outside of the imaging volume. In some implementations, the imaging volume is enclosed by EMI detectors 315.

The coils of the EMI detectors 315 may be mechanically adjusted to reduce induction between the EMI detectors and the RF TX coils 308 and/or MRI signal reception coils 310. The angle between the axis of the coils of the EMI detectors and the direction of the static magnetic field may be close to 90 degrees. In some implementations, the configuration of the coils of the EMI detectors may be similar to at least one of the configurations of the MRI signal receiving coils. In other implementations, the coils of the EMI detectors may be different from the MRI signal receiving coils in coil number, coil size, loop number and decoupling.

The magnet bore 313 of the system 300 may be sufficiently large to fit all or a portion of a human and has the same dimensions as described for magnet bore 313 in FIG. 1. The magnet bore 313 of the portable system may be spaced apart from an exterior 314 by walls of the portable system 100. A computing device 316 is connected to the system 300 to control the system and provide feedback to a user and is designed in accordance with the implementation described in FIG. 2.

Figure 4:
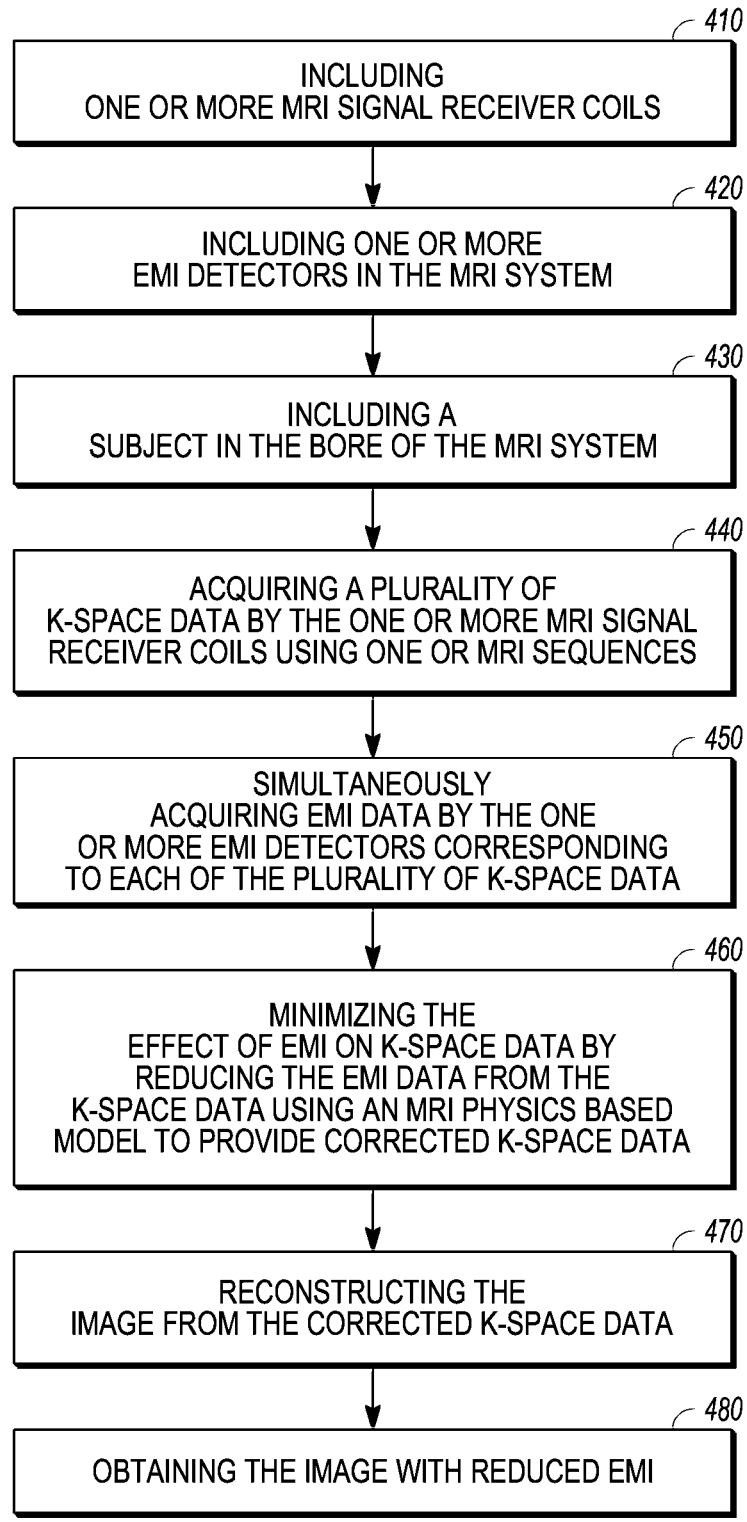
FIG. 4 is a flow chart illustrating a method for minimizing EMI in an MRI system at a given static magnetic field.

FIG. 4 is a flow chart where the steps of reducing EMI in an MRI system at a given static magnetic field are provided. At 410, one or more MRI signal receiving coils are included in the MRI system. At 420 one or more EMI detectors are included in the MRI system. The coils of the EMI detectors may be mechanically adjusted to reduce induction between the EMI detectors and the MRI signal receiving coils. The angle between the axis of the coils of the EMI detectors and the direction of the static magnetic field may be close to 90 degrees. In some implementations, the configuration of the coils of the EMI detectors adjacent to the MRI signal receiving coils may be similar to at least one of the configurations of the MRI signal receiving coils. In other implementations, the coils of the EMI detectors adjacent to the MRI signal receiving coils may be different from the MRI signal receiving coils in coil number, coil size, loop number and decoupling.

Referring now to 430, a subject is included in the bore of the MRI systems. In some implementations, the imaging volume of the subject will typically be enclosed by the EMI detectors. In other implementations, the EMI detectors are inside the imaging volume. In still other implementations, the EMI detectors are outside the imaging volume.

Referring now to 440, a plurality of k-space data for an image is acquired by the one or more MRI signal receiver coils using one or more MRI sequences. The MRI sequence generates an MRI signal which is collected by a receiver coil, amplified, and processed. The acquired measurements, which are collected in the spatial frequency domain, are digitized, and stored as complex numerical values in a "k-space" matrix. MRI sequences which may be used to acquire the plurality of k-space data for the image include, for example, a gradient echo sequence, a spin echo sequence, a fast gradient echo sequence, a fast spin echo sequence, and their variations with or without magnetization preparation or specific tissue suppression, parallel imaging technique, under-sampling technique, or administration of contrast agent.

Step 450 is simultaneous with step 440. Here at step 450, a plurality of EMI data corresponding to each of the plurality of k-space data collected at step 440 is acquired by the one or more EMI detectors. The EMI signal collected by the EMI detector is amplified and processed. The weight of each EMI signal is adjusted by its amplifier or mathematical model in the different MRI signal receiver coils. The EMI data, which is collected in the spatial frequency domain (i.e., k-space domain), is digitized, and stored as complex numerical values in a k-space matrix, which corresponds to each of the plurality of k-space data of the image for each receiver coil.

Figure 5:
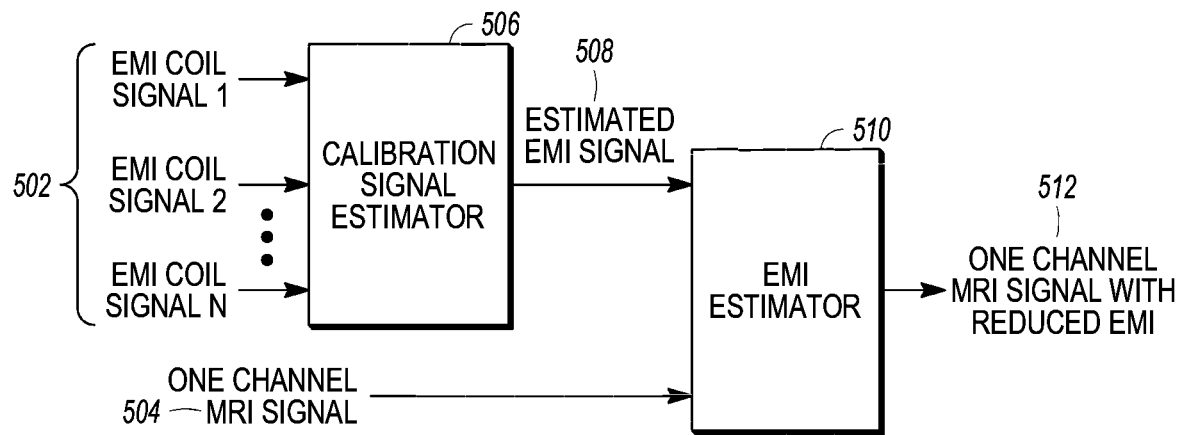
FIG. 5 illustrates an exemplary method for reducing EMI.

Referring now to 460 the effect of EMI on MRI k-space data is minimized by reducing the EMI data from the k-space data by using a MRI physics-based model to provide corrected k-space data. For example, the procedure summarized in FIG. 5 may be used to minimize the effect of EMI on the MRI k-space data.

In an exemplary deep learning method for reducing EMI in MRI system, EMI signals 502 collected by multiple conductive coils of EMI detectors are funneled into a calibration signal estimator 506, which provides an estimated EMI signal 508 that is contained in a one channel MRI signal 504 collected by a MRI signal receiving coil. One implementation of 506 trains a three-layer CNN model which relates the 1D temporal EMI signal 508 received by MRI signal receiving coil to the 1D temporal signals 502 received by multiple EMI coils.

The estimated EMI signal 508 and the one channel MRI signal 504 collected by a MRI signal receiving coil are sent to the EMI eliminator 510 which then minimizes the EMI contribution to provide a one channel MRI signal 512 with reduced EMI. Here, the estimated EMI signal 508 only corresponds to the one channel MRI signal 504. As for multiple receiver channels in the MRI system, multiple EMI signals are estimated, respectively. Another implementation of 510 could be a simple subtraction an estimated EMI signal 508 from the one channel MRI signal in the EMI eliminator 510.

Now at 370 the image is reconstructed, for example, by conventional methods such as by inverse 2D or 3D fast Fourier transform of the raw corrected k-space data. After the image is reconstructed, it may be transmitted to a display, for example, to provide an image with reduced EMI at 380.

In summary the method and system described herein provide a number of advantages. For, example, the static field strengths of the MRI system may vary from less than about 0.2 Tesla to about 7.0 Tesla in the system and methods described herein, Accordingly, the system and methods described herein may be used with electromagnetic and permanent MRI systems and superconducting MRI systems and thus the scope of the system and methods described herein includes mobile and non-mobile MRI systems in complex electromagnetic environments, particularly for complex electromagnetic environments, which are in enclosed in shielded locations. Complex electromagnetic environments may result from medical electronic devices (i.e., surgical robot, electric injector, etc.) which are adjacent to MRI systems in enclosed shielded locations. The system and methods described herein minimize EMI by an MRI physics-based model and distinguish the effect of different EMI on different MRI signals acquired by different sequences. These effects are evaluated by objective functions that are determined by the Bloch Equation and its variations. The system and methods described herein divide EMI into internal EMI and external EMI and minimize both internal EMI and external EMI. Additionally, the system and methods described herein use different methods (e.g., the size, the receiver bandwidth, sampling time, orientation, location, etc.) to sample internal EMI signals and external EMI signals.

The system and methods described herein evaluate the effect of EMI on the RF transmission in a MRI system, particularly when the EMI frequency is very close to the resonant frequency in the MRI systems. Accordingly, the system and methods described herein correct the effect of EMI on the RF transmission in an MRI system when the EMI frequency is very close to the resonant frequency in the MRI system. To achieve this goal, EMI detectors detect EMI signals during both radiofrequency transmission and reception in the system and methods described herein, thus better minimizing the effect of EMI in the k-space domain.

Finally, the trade-off between decoupling and correlation is a major challenge for minimizing the effect of EMI on an MRI signal. Hardware methods and/or software methods are used to decouple the interaction between EMI coils and MRI coils in the system and methods described herein.

Technical specialists skilled in the art should understand that, the implementations in this disclosure may be implemented as methods, systems, or computer program products. Therefore, this disclosure may be implemented in forms of a complete hardware implementation, a complete software implementation, and a combination of software and hardware implementation. Further, this disclosure may be embodied as a form of one or more computer program products which are embodied as computer executable program codes in computer writable storage media (including but not limited to disk storage and optical storage).

This disclosure is described in accordance with the methods, devices (systems), and flowcharts and/or block diagrams of computer program products of the implementations, which should be comprehended as each flow and/or block of the flowcharts and/or block diagrams implemented by computer program instructions, and the combinations of flows and/or blocks in the flowcharts and/or block diagrams. The computer program instructions therein may be provided to generic computers, special-purpose computers, embedded computers or other processors of programmable data processing devices to produce a machine, wherein the instructions executed by the computers or the other processors of programmable data processing devices produce an apparatus for implementing the functions designated by one or more flows in the flowcharts and/or one or more blocks in the block diagrams.

The computer program instructions may be also stored in a computer readable storage which is able to boot a computer or other programmable data processing device to a specific work mode, wherein the instructions stored in the computer readable storage produce a manufactured product containing the instruction devices which implements the functions designated by one or more flows in the flowcharts and/or one or more blocks in the block diagrams.

The computer program instructions may also be loaded to a computer or another programmable data processing device to execute a series of operating procedures in the computer or the other programmable data processing device to produce a process implemented by the computer, whereby the computer program instructions executed in the computer or the other programmable data processing device provide the operating procedures for the functions designated by one or more flows in the flowcharts and/or one or more blocks in the block diagrams.

Apparently, the technical specialists skilled in the art may perform any variation and/or modification to this disclosure by the principles and within the scope of this disclosure. Therefore, if the variations and modifications herein are within the scope of the claims and other equivalent techniques herein, this disclosure intends to include the variations and modifications thereof.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. The terms "at least one of A or B," "at least one of A and B," "one or more of A or B," "A and/or B" used herein mean "A", or "B" or "A and B".

While the disclosure has been described in connection with certain embodiments or implementations, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. An MRI system for minimizing EMI in an image acquired by the MRI system comprising:
   a magnet;
   one or more RF gradient coils;
   one or more MM signal receiving coils;
   one or more EMI detectors located inside an imaging volume, the one or more EMI detectors including electrically conductive coils adjacent to at least one of the RF gradient coils or the MRI signal receiving coils; and
   a computing device configured to execute instructions to:
   acquire a plurality of k-space data by the one or more MRI signal receiving coils using one or more MRI sequences;

simultaneously acquire EMI data from the one or more EMI detectors corresponding to each of the plurality of k-space data;

minimize the effect of EMI on the k-space data of the image by reducing the EMI data from the k-space data using an MRI physics-based model to provide corrected k-space data;

reconstruct the image from the corrected k-space data; and obtain the image with minimized EMI.

2. The system of claim 1, wherein the EMI is an internal EMI resulted from electronic devices inside an electromagnetically shielded room.

3. The system of claim 1, wherein the MRI system includes a superconducting magnet.

4. The system of claim 1, wherein the MRI system is portable, mobile, or stationary.

5. The system of claim 1, wherein the one or more EMI detectors adjacent to the MRI signal receiving coils include at least one EMI detector inside of the imaging volume and at least one EMI detector outside of the imaging volume.

6. The system of claim 1, wherein the static magnetic strength of the MRI system is less than about 7.0 Tesla.

7. The system of claim 1, wherein the coils of the EMI detector adjacent to the MRI signal receiving coils are different from at least one of the MRI signal receiving coils in coil number, coil size, loop number or decoupling.

8. The system of claim 1, wherein the MRI physics-based model is determined by the Bloch Equation and its variations.

9. The system of claim 1, wherein the MRI physics-based model is a neural network which comprises instructions executable by the computing device to:

pre-scan the EMI k-space data and MRI k-space data for a phantom;

apply a general neural network model for minimizing EMI;

refine the general neural network model using transfer learning and the data from pre-scanning to obtain an optimal neural network model; and minimize the effect of EMI by the optimal neural network model.

10. The system of claim 1, wherein the imaging volume is enclosed by the EMI detectors.

11. The system of claim 1, wherein the frequencies of the EMI data are similar to the Larmor frequencies.

12. The system of claim 11, wherein the frequencies are between about 1.0 MHz and about 960 MHz.

13. The system of claim 1, wherein the EMI data comprises at least one of internal EMI data and external EMI data.

14. The system of claim 13, wherein external EMI data is minimized by real time EMI data.

15. The system of claim 1, wherein the subject is a mammal, a human, an object or a phantom.

16. A method for minimizing electromagnetic interference (EMI) in an image acquired by a MRI system at a static magnetic field, the MRI system including one or more gradient coils, one or more MRI signal receiving coils, and one or more EMI detectors located inside an imaging volume, the one or more EMI detectors including electrically conductive coils adjacent to at least one of the gradient coils or the MRI signal receiving coils, the method comprising:

acquiring a plurality of k-space data of the subject by the one or more MRI signal receiver coils using one or more Mill sequences;

simultaneously acquiring EMI data by the one or more EMI detectors corresponding to each of the plurality of k-space data;

minimizing the effect of EMI on the k-space data by reducing the EMI data from the k-space data using an MRI physics-based model to provide corrected k-space data;

reconstructing the image from the corrected k-space data; and obtaining the image with minimized EMI.

17. The method of claim 16, wherein the EMI is an internal EMI resulted from electronic devices inside an electromagnetically shielded room.

18. The method of claim 16, wherein the magnet is a superconducting magnet.

19. The method of claim 16, wherein the MRI physics-based model is determined by the Bloch Equation and its variations.

20. The method of claim 16, wherein the MRI physics-based model is a neural network, the method further comprising:

pre-scanning the EMI k-space data and MRI k-space data for a phantom;

applying a general neural network model for minimizing EMI;

refining the general neural network model using transfer learning and the data from pre-scanning to obtain an optimal neural network model; and minimizing the effect of EMI by the optimal neural network model.

* * * * *